US008557861B2

(12) United States Patent
Chen

(10) Patent No.: US 8,557,861 B2
(45) Date of Patent: Oct. 15, 2013

(54) LOW OIL EMULSION COMPOSITIONS FOR DELIVERING TAXOIDS AND OTHER INSOLUBLE DRUGS

(75) Inventor: Andrew Xian Chen, San Diego, CA (US)

(73) Assignee: Mast Therapeutics, Inc., San Diego, CA (US)

(*) Notice: Subject to any disclaimer, the term of this patent is extended or adjusted under 35 U.S.C. 154(b) by 1375 days.

(21) Appl. No.: 10/952,243

(22) Filed: Sep. 28, 2004

(65) Prior Publication Data

US 2006/0067952 A1 Mar. 30, 2006

(51) Int. Cl.
*A61K 9/107* (2006.01)
*A61K 9/00* (2006.01)
*A61K 31/337* (2006.01)

(52) U.S. Cl.
USPC ............. 514/449; 516/53; 516/56; 516/73; 424/400

(58) Field of Classification Search
None
See application file for complete search history.

(56) References Cited

U.S. PATENT DOCUMENTS

| | | | |
|---|---|---|---|
| RE32,393 E | 4/1987 | Wretlind et al. ............ 514/219 |
| 4,816,247 A | 3/1989 | Desai et al. ................ 424/80 |
| 5,415,869 A | 5/1995 | Straubinger et al. ........ 424/450 |
| 5,439,686 A | 8/1995 | Desai et al. ............... 424/451 |
| 5,478,860 A | 12/1995 | Wheeler et al. ............ 514/449 |
| 5,616,330 A | 4/1997 | Kaufman et al. ........... 424/400 |
| 5,621,001 A | 4/1997 | Canetta et al. ............. 514/449 |
| 5,635,491 A | 6/1997 | Seki et al. ................. 514/53 |
| 5,641,803 A | 6/1997 | Carretta et al. ............ 514/449 |
| 5,665,761 A | 9/1997 | Canetta et al. ............. 514/449 |
| 5,670,536 A | 9/1997 | Durr et al. |
| 5,670,537 A | 9/1997 | Canetta et al. ............. 514/449 |
| 5,714,520 A | 2/1998 | Jones et al. ............... 514/731 |
| 5,750,142 A * | 5/1998 | Friedman et al. ........... 424/450 |
| 5,919,815 A | 7/1999 | Bradley et al. ............. 514/449 |
| 5,977,172 A | 11/1999 | Yoshikawa et al. ......... 514/530 |
| 6,028,108 A | 2/2000 | George ..................... 514/564 |
| 6,136,846 A | 10/2000 | Rubinfeld et al. |
| 6,140,373 A | 10/2000 | May et al. ................. 514/731 |
| 6,231,600 B1 | 5/2001 | Zhong ...................... 623/1.42 |
| 6,245,349 B1 | 6/2001 | Yiv et al. |
| 6,348,491 B1 | 2/2002 | Chu et al. ................. 514/449 |
| 6,414,014 B1 | 7/2002 | Canetta et al. ............. 514/449 |
| 6,455,280 B1 | 9/2002 | Edwards et al. ........... 435/69.1 |
| 6,458,373 B1 | 10/2002 | Lambert et al. ............ 424/405 |
| 6,469,069 B1 | 10/2002 | Mirejovsky et al. ........ 514/731 |
| 6,660,286 B1 | 12/2003 | Lambert et al. |
| 6,793,938 B2 | 9/2004 | Sankaram |
| 6,858,227 B1 | 2/2005 | Lal et al. |
| 6,906,101 B1 | 6/2005 | Bombardelli et al. |
| 6,979,456 B1 | 12/2005 | Parikh et al. |
| 7,030,155 B2 | 4/2006 | Lambert et al. |
| 7,223,770 B2 | 5/2007 | Zhang et al. |
| 7,786,164 B2 | 8/2010 | Zhang et al. |
| 2002/0006613 A1 | 1/2002 | Shyjan et al. .............. 435/6 |
| 2003/0065024 A1 | 4/2003 | Lambert et al. |
| 2003/0099674 A1 | 5/2003 | Chen ....................... 424/400 |
| 2005/0004002 A1 * | 1/2005 | Desai et al. ............... 514/2 |
| 2005/0077497 A1 | 4/2005 | Anderson |
| 2006/0008480 A1 | 1/2006 | Chen |
| 2006/0024360 A1 | 2/2006 | Chen |
| 2006/0067952 A1 | 3/2006 | Chen |

FOREIGN PATENT DOCUMENTS

| | | |
|---|---|---|
| DE | 198 43 968 A1 | 4/2000 |
| DE | 19900054 * | 6/2000 |
| EP | 1 097 715 A1 | 5/2001 |
| EP | 1 356 814 A1 | 10/2003 |
| EP | 1 510 206 A1 | 3/2005 |
| JP | H10-502921 A | 3/1998 |
| JP | H10-510267 A | 10/1998 |
| JP | 2000-509021 A | 7/2000 |
| JP | 2000-212067 A | 8/2000 |
| JP | 2005-225818 A | 8/2005 |
| WO | WO 96/02247 A1 | 2/1996 |
| WO | WO 96/17603 A1 | 6/1996 |
| WO | WO 97/36811 A1 | 10/1997 |
| WO | 99/04787 | 2/1999 |
| WO | WO 00/03724 A1 | 1/2000 |
| WO | WO 00/40236 A1 | 7/2000 |
| WO | WO 02/053154 A1 | 7/2002 |
| WO | WO 03/074027 A1 | 9/2003 |
| WO | WO 2005/065676 A1 | 7/2005 |
| WO | WO 2005/085677 A1 | 7/2005 |
| WO | WO 2006/015120 A2 | 2/2006 |

OTHER PUBLICATIONS

WO 0040236 (part- English translation).*
Translation of WO 00/40236 obtained from EPO website Apr. 13, 2009.*
EPO translation of WO 00/40236 (WO0040236_EPO_Trans.pdf).*
Supplementary EP Search Report, Aug. 7, 2012, EP application No. 05814192, 5 pages.

* cited by examiner

*Primary Examiner* — Kevin S Orwig
(74) *Attorney, Agent, or Firm* — Kilpatrick Townsend & Stockton LLP

(57) ABSTRACT

The present invention provides injectable oil-in-water emulsions of taxoid drugs or other water insoluble drugs. The present invention also provides methods for preparing and using such oil-in-water emulsions.

24 Claims, No Drawings

LOW OIL EMULSION COMPOSITIONS FOR DELIVERING TAXOIDS AND OTHER INSOLUBLE DRUGS

BACKGROUND OF THE INVENTION

1. Field of the Invention

The present invention relates to pharmaceutical compositions useful for parenteral administration of taxoid drugs or other insoluble drugs. More specifically, the present invention relates to injectable oil-in-water emulsions of taxoid drugs or other water insoluble drugs characterized as being low in oil content, small in droplet size, being stable, and being ready-to-use.

2. Description of the Related Art

Taxoid drugs are widely used in cancer chemotherapy. Because they tend to be highly toxic, taxoid drugs are almost always administered via injection or infusion of liquid solutions to better control their blood-borne concentrations. However, due to very high levels of insolubility of taxoid drugs, intravenous injection or infusion of these drugs poses serious problems and challenges for pharmaceutical scientists and physicians as well as serious side effects to the patient. Various methods for emulsifying, suspending, or encapsulating insoluble drugs in injectable formulations have been used for decades, but none of those approaches are fully satisfactory for taxoid drugs, and the "best available" formulations of paclitaxel and docetaxel drugs pose serious problems, risks, and drawbacks. Such problems include, for example, high rates of allergic and/or immune reactions, severe pain at injection sites, serious and potentially permanent damage to blood vessels at or near the site of injection.

Among all side effects, the allergic and/or immune reactions are the most serious and sometimes of fatal risk, and for that reason, the FDA has requested the manufacturers of paclitaxel and docetaxel to include a "black box" warning label for these products. For example, the "black box" warning for paclitaxel (TAXOL™) reads as follows:

"Anaphylaxis and severe hypersensitivity reactions characterized by dyspnea and hypotension requiring treatment, angioedema, and generalized urticaria have occurred in 2%-4% of patients receiving TAXOL™ in clinical trials. Fatal reactions have occurred in patients despite premedication. All patients should be pretreated with corticosteroids, diphenhydramine, and H2 antagonists."

The "black box" warning for docetaxel (TAXOTERE™) states:

"Severe hypersensitivity reactions characterized by hypotension and/or bronchospasm, or generalized rash/erythema occurred in 2.2% (2/92) of patients who received the recommended 3-day dexamethasone premedication. Hypersensitivity reactions requiring discontinuation of the TAXOTERE™ infusion were reported in five patients who did not receive premedication. These reactions resolved after discontinuation of the infusion and the administration of appropriate therapy. TAXOTERE™ must not be given to patients who have a history of severe hypersensitivity reactions to TAXOTERE™ or to other drugs formulated with polysorbate 80."

However, the severe adverse reactions of these two important drugs are not due to the drugs themselves, but to the inactive ingredients used in their formulations. For TAXOL™, the anaphylaxis and severe hypersensitivity are caused by Cremophor® EL (polyoxyethylated castor oil), and for TAXOTERE™, polysorbate 80.

It is therefore apparent that there exist serious limitations and shortcomings in the current state of the art for injecting insoluble taxoid drugs as well as for injecting other types of highly insoluble drugs.

SUMMARY OF THE INVENTION

The present invention provides pharmaceutical compositions for delivering taxoid drugs or other water insoluble drugs and methods for making and using such compositions. The compositions of the present invention have one or more of the following properties: (1) injectable, (2) in the form of an oil-in-water emulsion, (3) stable under appropriate storage conditions, (4) containing pharmaceutically effective amount of a taxoid drug or another water insoluble drug, (5) sterilizable by filtration, (6) containing components acceptable by regulatory agencies (e.g., the FDA), (7) containing low oil content and thus not causing hyperlipidemia, and (8) not hyperallergenic or vein irritating.

In one aspect, the present invention provides an injectable oil-in-water emulsion that comprises, or consists essentially of, (a) a pharmaceutically effective amount of a taxoid drug or another water insoluble drug, (2) an oil component at a concentration of at most about 6% by weight, (c) a phospholipid component at a concentration of between about 1.2% to 5% by weight, and (d) water.

In certain embodiments, the emulsion contains a taxoid at a concentration at least about 0.02%, 0.03%, 0.04%, 0.05%, 0.06%, 0.07%, 0.08%, 0.09%, or 0.1% by weight.

In certain embodiments, the taxoid drug is paclitaxel or docetaxel.

In certain embodiments, the oil component comprises a vegetable oil.

In certain embodiments, the oil component comprises a vegetable oil and a medium chain triglycerol. In certain embodiments, the weight ratio of the vegetable oil to the medium chain triglycerol is about 9:1 to about 1:1.

In certain embodiments, the emulsion further comprises a stabilizer, such as glycine and EDTA.

In certain embodiments, the emulsion further comprises a tonicity modifier, such as glycerol.

In certain embodiments, the average size of the oil droplets in the emulsion is less than about 500 nm, 400 nm, 300 nm, 200 nm, 150 nm or 100 nm.

In another aspect, the present invention provides an injectable oil-in-water emulsion that comprises, or consists essentially of, (a) a taxoid drug at a concentration of about 0.03% or higher by weight, (b) a medium chain triglyceride (e.g., Miglyol 812) at a concentration of about 1% to about 3% by weight, (c) a vegetable oil (e.g., soybean oil) at a concentration of about 1% to about 3% by weight, (d) a phospholipid (e.g., soy lecithin or egg lecithin) at a concentration of about 1% to about 5% by weight, and (e) water.

In certain embodiments, the emulsion may further comprise glycine at a concentration of about 0.5% to about 1%, a tonicity modifier (e.g., a glycerol) at a concentration of about 1.5% to 2.5%, and/or EDTA at a concentration of about 0.005%.

In another aspect, the present invention provides an injectable oil-in-water emulsion that comprises, or consists essentially of, (a) a taxoid drug or another water insoluble drug at a therapeutically effective concentration, (b) an oil component, (c) an emulsifier, and (d) water, wherein the emulsion is stable for at least 6 months.

In certain embodiments, the emulsifier is a phospholipid.

In certain embodiments, the emulsion may be directly injected without need for a dilution.

In certain embodiments, some or all of the individual components of the emulsion other than the taxoid drug or the water insoluble drug are generally regarded as safe for use in intravenous injections by a drug regulatory authority.

In certain embodiments, the injectable emulsion is not hyperallergenic or vein irritating.

In certain embodiments, the average size of the oil droplets in the emulsion does not increase more than 25% after storage at about 2-8° C. for at least 6 months.

In certain embodiments, the concentration of the taxoid drug in the emulsion does not decrease by more than 10% after storage at about 2-8° C. for 6 months.

In certain embodiments, the emulsion does not comprise a cryoprotectant.

In certain embodiments, the emulsion does not comprise a cryoprotectant component in an amount sufficient for stabilizing the oil droplets of the emulsion during lyophilization (e.g., an amount sufficient for allowing the average droplet size of the rehydrated emulsion to be no more than about 200% of the average droplet size of the emulsion before the freeze-drying).

In certain embodiments, the emulsion does not comprise one or any of the group consisting of aliphatic or aromatic acids, amines, polyethylene glycol-linked lipids, propylene glycols, polyethylene glycols, non-ionic surfactants, polyethyleneglycol-modified phosphatidylethanolamines, tocopherols, tocotrienols, and derivatives of tocopherols and tocotrienols.

In another aspect, the present invention also provides a method for preparing an injectable oil-in-water emulsion that contains a pharmaceutically effective amount of a taxoid drug or another water insoluble drug. The method comprises (a) forming a mixture that comprises appropriate amounts of (i) a taxoid drug, (ii) an oil component (e.g., a vegetable oil, or a combination of a vegetable oil and a medium chain triglyceride), and (iii) a phospholipid, and (b) forming an oil-in-water emulsion with the mixture of step (a) and an aqueous solution.

In certain embodiments, the taxoid drug is docetaxel or paclitaxel.

In certain embodiments, the method further comprises (c) adjusting the pH of the emulsion to about 3.5 to about 7.0 for docetaxel, or to about 6 to about 7 for paclitaxel.

In certain embodiments, step (a) may be performed by dissolving the taxoid drug or the other water insoluble drug in a solution (e.g., ethanol) and mixing the dissolved taxoid drug or the dissolved water insoluble drug with a composition that comprises the oil component and the phospholipid.

In certain embodiments, step (b) may be performed by adding the aqueous solution to the mixture of step (a) via mechanical homogenization.

In another aspect, the present invention also provides a method of treating cancer by administering to a subject in need thereof a pharmaceutically effective amount of an injectable oil-in-water emulsion described herein that comprises a taxoid drug.

In certain embodiments, the administration may be intravenous, intramuscular, intra-arterial, intrathecal, intraocular, subcutaneous, intraarticular and intra-peritoneal.

DETAILED DESCRIPTION OF THE INVENTION

The present invention, in one aspect, provides pharmaceutical compositions for delivering taxoid drugs and other water insoluble drugs. Such compositions are oil-in-water emulsions that comprise a taxoid drug or another water insoluble drug, an oil component, an emulsifier (e.g., a phospholipid component), and water. Optionally, these compositions may further comprise a stabilizer or a tonicity modifier. The compositions of the present invention have one or more of the following properties: (1) injectable, (2) stable under appropriate storage conditions, (3) containing a pharmaceutically effective amount of a taxoid drug or another water insoluble drug, (4) sterilizable by filtration, (5) containing components acceptable by regulatory agencies (e.g., the FDA), (6) containing low oil content and thus not causing hyperlipodemia, and (7) not hyperallergenic or vein irritating.

The compositions of the present invention differ from emulsions disclosed in the art for parenterally delivering drugs at least in their oil concentrations. More specifically, nearly all emulsions in the art contain high oil concentrations, typically at 10%, 15% or sometimes 20%. These emulsions are herein referred to as the "high oil emulsions." High oil emulsions may pose the following major problems and drawbacks.

(1) Instability of the emulsion due to droplet aggregation. The high oil content produces an emulsion with high droplet density (i.e., the number of droplet per volume unit). A high droplet density will increase the chance for the droplets to bombard into each other and thus increase the chance of aggregation.

(2) Large droplet size. A high oil emulsion tends to have large droplets (more than 200 nm in diameter). Most commercial parenteral emulsion products (nutritional fat emulsions) contain droplets with average size from about 300 nm to about 400 nm and cannot be filtrated through a 0.2-micron filter. However, some heat sensitive drugs such as the taxoid drugs must be sterilized by filtrating through 0.2-micron membranes.

(3) Hyperlipidemia may result from the excessive intake of the oil from a high oil emulsion.

An "oil-in-water emulsion" refers to a colloidal dispersion system in which liquid oil is dispersed in small droplets (the discrete phase, also referred to as "the oil phase") in an aqueous medium (the continuous phase, also referred to as "the aqueous phase").

In certain embodiments, greater than 60%, 65%, 70%, 75%, 80%, 85%, 90%, 92%, 94%, 95%, 96%, 97%, 98%, or 99% of a taxoid drug or another water insoluble drug is present in the oil phase.

"Taxines" refers to a class of anticancer compounds, several of which are widely used in cancer chemotherapy. The primary example is known as TAXOL™, the trade name given to an injectable formulation that contains an anticancer compound called paclitaxel. Another Taxoid drug is docetaxel with a trade name of TAXOTERE™.

Paclitaxel is normally obtained via a semi-synthetic process from *Taxus baccata*. The chemical name for paclitaxel is 5β,20-epoxy-1,2α,4,7β,10β,13α-hexahydroxytax-11-en-9-one 4,10-diacetate 2-benzoate 13-ester with (2R,3S)-N-benzoyl-3-phenylisoserine. Paclitaxel has the following structural formula:

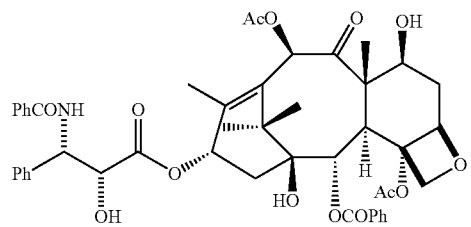

Paclitaxel is highly lipophilic and insoluble in water.

Docetaxel is prepared by semisynthesis beginning with a precursor extracted from the renewable needle biomass of yew plants. The chemical name for docetaxel is (2R,3S)-N-carboxy-3-phenylisoserine,N-tert-butyl ester, 13-ester with 5(beta)-20-epoxy-1,2(alpha),4,7(beta), 10(beta),13(alpha)-hexahydroxytax-11-en-9-one 4-acetate 2-benzoate, trihydrate. Docetaxel has the following structural formula:

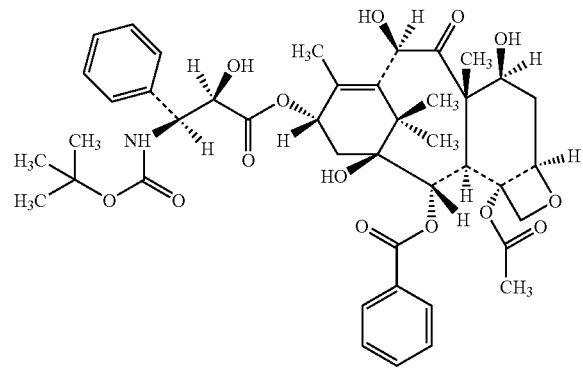

Docetaxel is also highly lipophilic and practically insoluble in water.

Because synthetic chemists and other researchers have developed numerous analogs and derivatives of taxine compounds, and since it is not always clear whether a particular analog or derivative falls within the formal definition of "taxine" compounds, the term "taxoid drugs" is used herein to include taxines as well as isomers, analogs, and derivatives of taxines that have molecular structures similar to taxines. However, to be included within the term "taxoid drugs" as used herein, a taxine drug, or an isomer, analog, or derivative of a taxine drug, must be pharmacologically acceptable and have a therapeutic medical utility in injectable formulations. Examples of water-insoluble taxoids that have been commercially used or reported in the scientific literature as having anti-cancer activities include, but are not limited to, paclitaxel; docetaxel; taxane; spicatin; yunnanxol; taxane-2,13-dione,5.beta.,9.beta.,10.beta.-trihydroxy-cyclic-9,10-acetal with acetone or acetate; taxane-2,13-dione,5.beta.,9.beta.,10.beta.-trihy-droxy-cyclic-9,10-acetal with acetone or acetate; taxane-2.beta.,15.beta.,-9.beta.,10.beta.-tetrol-cyclic-9,10-acetal with acetone or acetate; N-debenzoylPaclitaxel A; cephalomannine; cephalomannine-7-xyloside; 7-epi-10-deacetyl-cephalomannine; 10-deacetyl-cephalomannine; baccatin; baccatin diacetate; baccatin I through VI; 7-epi-baccatin III; baccatin A; 7-(4-azido-benzoyl)-baccatin III; O-acetylbaccatin IV; 7-(triethylsilyl)-baccatin III; 7,10-di-O-[(2,2,2-trichloroethoxy)-carbon-yl]-baccatin III; 13-(2', 3'-dihydroxy-3'-phenylpropionyl)-baccatin III; baccatin III 13-O-acetate; Paclitaxel B; epiPaclitaxel; 10-deacetyl-7-epi-Paclitaxel; 10-deacetylPaclitaxel; 10-deacetylPaclitaxel B or C; 7-xylosyl-10-deacetylPaclitaxel; and 10-deacetylPaclitaxel-7-xyloside.

The term "insoluble" refers to the lack of solubility of a taxoid or another drug in aqueous solutions (such as water, physiological saline, injectable dextrose solutions, etc). The USP/NF generally expresses the solubility in terms of the volume of solvent required to dissolve 1 gram of the drug at a specified temperature (e.g., 1 g aspirin in 300 ml $H_2O$, 5 ml ethanol at 25° C.). Other references may use more subjective terms to describe solubility, such as those given in the following table from Remington's Pharmaceutical Sciences, Mack Publishing Co., Easton, Pa., latest edition.

| Descriptive terms | Parts of solvent needed for 1 part solute |
|---|---|
| Very soluble | <1 |
| Freely soluble | 1-10 |
| Soluble | 10-30 |
| Sparingly soluble | 30-100 |
| Slightly soluble | 100-1000 |
| Very slightly soluble | 1000-10,000 |
| Practically insoluble or insoluble | >10,000 |

Therefore, the "water insoluble drugs" of this invention include the drugs in the bottom four solubility categories, i.e., "sparingly soluble," "slightly soluble," "very slightly soluble," and "practically insoluble or insoluble" when water is used as the solvent.

The term "insoluble" may be used interchangeably with hydrophobic, lipophilic, oleophilic, and similar terms. Both paclitaxel and docetaxel are insoluble drugs.

As indicated above, the present application also provides pharmaceutical compositions for delivering water insoluble drugs other than taxoid drugs. Such drugs include, but are not limited to, pharmaceutically active agents, diagnostic agents, agents of nutritional value, and the like. Examples of water insoluble drugs include:

Analgesics/antipyretics (e.g., aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, oxycodone hydrochloride, codeine phosphate, dihydrocodeine bitartrate, pentazocine hydrochloride, hydrocodone bitartrate, levorphanol tartrate, diflunisal, trolamine salicylate, nalbuphine hydrochloride, mefenamic acid, butorphanol tartrate, choline salicylate, butalbital, phenyltoloxamine citrate, diphenhydramine citrate, methotrimeprazine, cinnamedrine hydrochloride, meprobamate, and the like);

Anesthetics (e.g., cyclopropane, enflurane, halothane, isoflurane, methoxyflurane, nitrous oxide, propofol, and the like);

Antiasthmatics (e.g., Azelastine, Ketotifen, Traxanox, and the like);

Antibiotics (e.g., neomycin, streptomycin, chloramphenicol, cephalosporin, ampicillin, penicillin, tetracycline, and the like);

Aantidepressants (e.g., nefopam, oxypertine, doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, desipramine hydrochloride, trimipramine maleate, protriptyline hydrochloride, and the like);

Antidiabetics (e.g., biguanides, hormones, sulfonylurea derivatives, and the like);

Antifungal agents (e.g., griseofulvin, keloconazole, amphotericin B, Nystatin, candicidin, and the like);

Antihypertensive agents (e.g., propanolol, propafenone, oxyprenolol, Nifedipine, reserpine, trimethaphan camsylate, phenoxybenzamine hydrochloride, pargyline hydrochloride, deserpidine, diazoxide, guanethidine monosulfate, minoxidil, rescinnamine, sodium nitroprusside, rauwolfia serpentina, alseroxylon, phentolamine mesylate, reserpine, and the like);

Anti-inflammatories (e.g., (non-steroidal) indomethacin, naproxen, ibuprofen, ramifenazone, piroxicam, (steroidal) cortisone, dexamethasone, fluazacort, hydrocortisone, prednisolone, prednisone, and the like);

Antineoplastics (e.g., adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxanes and derivatives thereof (e.g., paclitaxel and derivatives thereof, taxotere and derivatives thereof, and the like), vinblastine, vincristine, tamoxifen, piposulfan, and the like);

Antianxiety agents (e.g., lorazepam, buspirone hydrochloride, prazepam, chlordiazepoxide hydrochloride, oxazepam, clorazepate dipotassium, diazepam, hydroxyzine pamoate, hydroxyzine hydrochloride, alprazolam, droperidol, halazepam, chlormezanone, dantrolene, and the like);

Immunosuppressive agents (e.g., cyclosporine, azathioprine, mizoribine, FK506 (tacrolimus), and the like);

Antimigraine agents (e.g., ergotamine tartrate, propanolol hydrochloride, isometheptene mucate, dichloralphenazone, and the like);

Sedatives/hypnotics (e.g., barbiturates (e.g., pentobarbital, pentobarbital sodium, secobarbital sodium, and the like), benzodiazapines (e.g., flurazepam hydrochloride, triazolam, tomazeparm, midazolam hydrochloride, and the like), and the like);

Antianginal agents (e.g., beta-adrenergic blockers, calcium channel blockers (e.g., nifedipine, diltiazem hydrochloride, and the like), nitrates (e.g., nitroglycerin, isosorbide dinitrate, pentaerythritol tetranitrate, erythrityl tetranitrate, and the like), and the like);

Antipsychotic agents (e.g., haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, and the like);

Antimanic agents (e.g., lithium carbonate, and the like);

Antiarrhythmics (e.g., bretylium tosylate, esmolol hydrochloride, verapamil hydrochloride, amiodarone, encainide hydrochloride, digoxin, digitoxin, mexiletine hydrochloride, disopyramide phosphate, procainamide hydrochloride, quinidine sulfate, quinidine gluconate, quinidine polygalacturonate, flecainide acetate, tocainide hydrochloride, lidocaine hydrochloride, and the like);

Antiarthritic agents (e.g., phenylbutazone, sulindac, penicillamine, salsalate, piroxicam, azathioprine, indomethacin, meclofenamate sodium, gold sodium thiomalate, ketoprofen, auranofin, aurothioglucose, tolmetin sodium, and the like);

Antigout agents (e.g., colchicine, allopurinol, and the like);

Anticoagulants (e.g., heparin, heparin sodium, warfarin sodium, and the like);

Thrombolytic agents (e.g., urokinase, streptokinase, altoplase, and the like);

Antifibrinolytic agents (e.g., aminocaproic acid, and the like);

Hemorheologic agents (e.g., pentoxifylline, and the like);

Antiplatelet agents (e.g., aspirin, empirin, ascriptin, and the like);

Anticonvulsants (e.g., valproic acid, divalproate sodium, phenytoin, phenytoin sodium, clonazepam, primidone, phenobarbitol, phenobarbitol sodium, carbamazepine, amobarbital sodium, methsuximide, metharbital, mephobarbital, mephenytoin, phensuximide, paramethadione, ethotoin, phenacemide, secobarbitol sodium, clorazepate dipotassium, trimethadione, and the like);

Antiparkinson agents (e.g., ethosuximide, and the like);

Antihistamines/antipruritics (e.g., hydroxyzine hydrochloride, diphenhydramine hydrochloride, chlorpheniramine maleate, brompheniramine maleate, cyproheptadine hydrochloride, terfenadine, clemastine fumarate, triprolidine hydrochloride, carbinoxamine maleate, diphenylpyraline hydrochloride, phenindamine tartrate, azatadine maleate, tripelennamine hydrochloride, dexchlorpheniramine maleate, methdilazine hydrochloride, trimprazine tartrate, and the like);

Agents useful for calcium regulation (e.g., calcitonin, parathyroid hormone, and the like);

Antibacterial agents (e.g., amikacin sulfate, aztreonam, chloramphenicol, chloramphenicol palmitate, chloramphenicol sodium succinate, ciprofloxacin hydrochloride, clindamycin hydrochloride, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, colistin sulfate, and the like);

Antiviral agents (e.g., interferon gamma, zidovudine, amantadine hydrochloride, ribavirin, acyclovir, and the like);

Antimicrobials (e.g., cephalosporins (e.g., cefazolin sodium, cephradine, cefaclor, cephapirin sodium, ceftizoxime sodium, cefoperazone sodium, cefotetan disodium, cefutoxime azotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, and the like), and the like);

Bronchodialators (e.g., sympathomimetics (e.g., epinephrine hydrochloride, metaproterenol sulfate, terbutaline sulfate, isoetharine, isoetharine mesylate, isoetharine hydrochloride, albuterol sulfate, albuterol, bitolterol, mesylate isoproterenol hydrochloride, terbutaline sulfate, epinephrine bitartrate, metaproterenol sulfate, epinephrine, epinephrine bitartrate, and the like), anticholinergic agents (e.g., ipratropium bromide, and the like), xanthines (e.g., aminophylline, dyphylline, metaproterenol sulfate, aminophylline, and the like), mast cell stabilizers (e.g., cromolyn sodium, and the like), inhalant corticosteroids (e.g., flurisolidebeclomethasone dipropionate, beclomethasone dipropionate monohydrate, and the like), salbutamol, beclomethasone dipropionate (BDP), ipratropium bromide, budesonide, ketotifen, salmeterol, xinafoate, terbutaline sulfate, triamcinolone, theophylline, nedocromil sodium, metaproterenol sulfate, albuterol, flunisolide, and the like);

Hormones (e.g., androgens (e.g., danazol, testosterone cypionate, fluoxymesterone, ethyltostosterone, testosterone enanihate, methyltestosterone, fluoxymesterone, testosterone cypionate, and the like), estrogens (e.g., estradiol, estropipate, conjugated estrogens, and the like), progestins (e.g., methoxyprogesterone acetate, norethindrone acetate, and the like), corticosteroids (e.g., triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate methylprednisolone sodium succinate, hydrocortisone sodium succinate, methylprednisolone sodium succinate, triamcinolone hexacatonide, hydrocortisone, hydrocortisone cypionate, prednisolone, fluorocortisone acetate, paramethasone acetate, prednisolone tebulate, prednisolone acetate, prednisolone sodium phosphate, hydrocortisone sodium succinate, and the like), thyroid hormones (e.g., levothyroxine sodium, and the like), and the like;

Hypoglycemic agents (e.g., human insulin, purified beef insulin, purified pork insulin, glyburide, chlorpropamide, glipizide, tolbutamide, tolazamide, and the like);

Hypolipidemic agents (e.g., clofibrate, dextrothyroxine sodium, probucol, lovastatin, niacin, and the like);

Agents useful for erythropoiesis stimulation (e.g., erythropoietin, and the like);

Antiulcer/antireflux agents (e.g., famotidine, cimetidine, ranitidine hydrochloride, and the like);

Antinauseants/antiemetics (e.g., meclizine hydrochloride, nabilone, prochlorperazine, dimenhydrinate, promethazine hydrochloride, thiethylperazine, scopolamine, and the like);

Oil-soluble vitamins (e.g., vitamins A, D, E, K, and the like);

As well as other drugs such as mitotane, visadine, halonitrosoureas, anthrocyclines, ellipticine, and the like.

Additional examples of pharmaceutically active agents include those compounds which are substantially water insoluble and which are listed in the "Therapeutic Category and Biological Activity Index" of The Merck Index (12th Ed'n, 1996), the entire relevant contents of which are hereby incorporated by reference.

Examples of diagnostic agents contemplated for use in the practice of the present invention include ultrasound contrast agents, radiocontrast agents (e.g., iodo-octanes, halocarbons, renografin, and the like), magnetic contrast agents (e.g., fluorocarbons, lipid soluble paramagnetic compounds, and the like), as well as other diagnostic agents which cannot readily be delivered without some physical and/or chemical modification to accommodate the substantially water insoluble nature thereof.

Examples of agents of nutritional value contemplated for use in the practice of the present invention include amino acids, sugars, proteins, carbohydrates, fat-soluble vitamins (e.g., vitamins A, D, E, K, and the like) or fat, or combinations of any two or more thereof.

"Therapeutically effective concentration" (used exchangeable with "pharmaceutically effective concentration") refers to the concentration of a drug (e.g., paclitaxel) that is effective to treat diseases or disorders (e.g., cancer), at a reasonable benefit/risk ratio applicable to any medical treatment. Exemplary therapeutically effective concentrations of taxoid drugs include, but are not limited to, from about 0.1 mg/mL to about 0.5 mg/mL (or about 0.01% to about 0.05%).

"Concentration by weight," as used herein, refers to the ratio (in percentage) of the weight of a component (e.g., a taxoid drug) of a composition (e.g., a low-oil emulsion) to the total weight of the composition, if not otherwise noted.

The term "oil" is used herein in a general sense to identify hydrocarbon derivatives, carbohydrate derivatives, or similar organic compounds that are liquid at body temperatures, e.g., about 37° C., and are pharmacologically acceptable in injectable formulations. It includes glycerides or non-glycerides.

The term "oil component" or "oil phase" refers to an oil, or a combination of multiple oils.

In certain embodiments, the oil component of the present invention comprises a monoglyceride, a diglyceride, a triglyceride, or a mixture thereof. In certain embodiments, the oil component comprises an ester formed between one or more fatty acids and an alcohol other than glycerol.

In certain embodiments, the oil refers to a "vegetable oil". Vegetable oil refers to oil derived from plant seeds or nuts. Exemplary vegetable oils include, but are not limited to, almond oil, borage oil, black currant seed oil, corn oil, safflower oil, soybean oil, sesame oil, cottonseed oil, peanut oil, olive oil, rapeseed oil, coconut oil, palm oil, canola oil, etc. Vegetable oils are typically "long-chain triglycerides," formed when three fatty acids (usually about 14 to about 22 carbons in length, with unsaturated bonds in varying numbers and locations, depending on the source of the oil) form ester bonds with the three hydroxyl groups on glycerol. In certain embodiments, vegetable oils of highly purified grade (also called "super refined") are generally used to ensure safety and stability of oil-in-water emulsions. In certain embodiments, hydrogenated vegetable oils, which are produced by controlled hydrogenation of the vegetable oil, may be used in the present invention.

In certain embodiments, the oil refers to "medium chain triglycerides". Medium chain triglycerides (MCT's) are another class of triglyceride oil that can be either naturally derived or synthetic. MCT's are made from fatty acids that are usually about 8 to about 12 carbons in length. Like vegetable oils, MCT's have been used extensively in emulsions designed for injection as a source of calories, for patients requiring parenteral nutrition. Such oil is commercially available as Miglyol 812 from SASOL GmbH, Germany, CRODAMOL GTCC-PN from Croda Inc. of Parsippany, N.J., or Neobees M-5 oil from PVO International, Inc., of Boonton, N.J. Other low-melting medium chain oils may also be used in the present invention.

"Animal fat" refers to oil derived from an animal source. It also comprises triglycerides, but the lengths of, and unsaturated bonds in, the three fatty acid chains vary, compared to vegetable oils. Animal fats from sources that are solid at room temperature (such as tallow, lard, etc.) can be processed to render them liquid if desired. Other types of animal fats that are inherently liquid at room temperature include various fish oils, etc.

In certain embodiments, the combinations of vegetable oil and MCT oil are used in the present invention. Such combinations generally have long record of safe use in combination in injectable emulsions and provide the superior stability for the colloidal dispersions or dry solid of this invention. The specific type of vegetable oil used (i.e., soy bean oil, corn oil, or safflower oil, etc.) is not critical, so long as it is safe, well tolerated, pharmaceutically acceptable, chemically stable and provides dispersion droplets having a desired size range.

The content of the total oil component in the emulsion of this invention may be within a range of about 1% to about 6%, by weight. In certain embodiments, the total concentration of the oil component is within a range of about 2% to about 4%. In certain embodiments, the total concentration of the oil component is about, or at most about, 1%, 2%, 3%, 4%, 5%, or 6% by weight. In certain embodiments, the emulsions comprise oil in an amount that does not result in hyperlipodemia when administered to a subject.

The low oil content in the emulsions of the present invention provides several advantages. First, it enables the preparation of emulsions with small droplet sizes (e.g., no more than 200 nm), which in turn allows for sterilization of the emulsions by filtration through a 0.2 µm filter as well as more freely circulation in an animal or human body that is subject to the administration of the emulsions. Second, the low oil content increases the stability of the emulsions. While not wishing to be bound by any particular theory, it is believed that the low oil content reduces the chance of oil droplets to coalesce and aggregate with each other. Third, the low oil content facilitates the preparation of the emulsions because the resulting emulsions are less viscous than those with higher oil contents.

In certain embodiments, the vegetable oil to MCT oil ratio in an emulsion within a range of about 9:1 to about 1:5, by weight. In certain embodiments, the ratio of the vegetable oil to MCT oil is within a range of about 2:1 to about 1:2 by weight. In certain embodiments, the weight ratio of the vegetable oil to MCT oil is about 9:1, 8:1, 7:1, 6:1, 5:1, 4:1, 3:1, 2:1, 1:1, 1:2, 1:3, 1:4 or 1:5.

The non-glycerides referred in this invention are chiefly cholesterol.

In certain embodiments, the oil component of a formulation of the present invention comprises soybean oil and MCT.

In certain embodiments, the weight ratio of a taxoid drug (or another insoluble drug) to the oil component (e.g., triglyceride) in the emulsions of this invention is about 1:20, 1:30, 1:40, 1:50, 1:60, 1:70, 1:80, 1:90, 1:100 or 1:120.

An "emulsifier" refers to a compound that prevents the separation of the injectable emulsion into individual oil and aqueous phases. Emulsifiers useful in the present invention generally are (1) compatible with the other ingredients of the oil-in-water emulsions of the present invention, (2) do not interfere with the stability or efficacy of the taxoid drug or another water insoluble drug in the emulsions, (3) are stable and does not deteriorate in the preparation, and (4) are non-toxic.

Suitable emulsifiers include, but are not limited to, propylene glycol mono- and di-fatty acid esters, polyoxyethylene sorbitan fatty acid esters, polyoxyethylene fatty acid esters, polyoxyethylene-polyoxypropylene co-polymers and block co-polymers, salts of fatty alcohol sulphates, sorbitan fatty acid esters, esters of polyethylene-glycol glycerol ethers, oil and wax based emulsifiers, glycerol monostearate, glycerine sorbitan fatty acid esters and phospholipids.

A "phospholipid component" refers to a pure phospholipid or a combination or mixture of two or more phospholipids A "phospholipid" refers to a triester of glycerol with two fatty acids and one phosphate ion. Exemplary phospholipids useful in the present invention include, but are not limited to, phosphatidyl chlorine, lecithin (a mixture of choline ester of phosphorylated diacylglyceride), phosphatidylethanolamine, phosphatidylglycerol, phosphatidic acid with about 4 to about 22 carbon atoms, and more generally from about 10 to about 18 carbon atoms and varying degrees of saturation. The phospholipid component of the drug delivery composition can be either a single phospholipid or a mixture of several phospholipids. The phospholipids should be acceptable for the chosen route of administration.

The phospholipids useful in the present invention can be of natural origin. Naturally occurring phospholipids include soy lecithin, egg lecithin, hydrogenated soy lecithin, hydrogenated egg lecithin, sphingosine, gangliosides, and phytosphingosine and combinations thereof.

Naturally occurring lecithin is a mixture of the diglycerides of stearic, palmitic, and oleic acids, linked to the choline ester of phosphoric acid, commonly called phosphatidylcholine, and can be obtained from a variety of sources such as eggs and soya beans. Soy lecithin and egg lecithin (including hydrogenated versions of these compounds) have a long history of safety, possess combined emulsification and solubilization properties, and tend to be broken down into innocuous substances more rapidly than most synthetic surfactants. Commercially available soya phospholipids are the Centrophase and Centrolex products marketed and sold by Central Soya, Phospholipon from Phospholipid GmbH, Germany, Lipoid by Lipoid GmbH, Germany, and EPIKURON by Degussa.

Hydrogenated lecithin is the product of controlled hydrogenation of lecithin. It may also be used in the present invention.

According to the United State Pharmacopoeia (USP), lecithin is a non-proprietary name describing a complex mixture of acetone-insoluble phospholipids, which consists chiefly of phosphotidylcholine, phosphotidylethanolamine, phosphotidylserine and phosphotidylinositol, combined with various amounts of other substances such as triglycerides, fatty acids, and carbohydrates.

Pharmaceutically, lecithins are mainly used as dispersing, emulsifying, and stabilizing agents and are included in intramuscular and intravenous injections, parenteral nutritional formulations and topical products. Lecithin is also listed in the FDA Inactive Ingredients Guide for use in inhalations, IM and IV injections, oral capsules, suspensions and tablets, rectal, topical, and vaginal preparations.

Phospholipids can also be synthesized and the common synthetic phospholipids are listed below:
Diacylglycerols
1,2-Dilauroyl-sn-glycerol (DLG)
1,2-Dimyristoyl-sn-glycerol (DMG)
1,2-Dipalmitoyl-sn-glycerol (DPG)
1,2-Distearoyl-sn-glycerol (DSG)
Phosphatidic Acids
1,2-Dimyristoyl-sn-glycero-3-phosphatidic acid, sodium salt (DMPA,Na)
1,2-Dipalmitoyl-sn-glycero-3-phosphatidic acid, sodium salt (DPPA,Na)
1,2-Distearoyl-sn-glycero-3-phosphatidic acid, sodium salt (DSPA,Na)
Phosphocholines
1,2-Dilauroyl-sn-glycero-3-phosphocholine (DLPC)
1,2-Dimyristoyl-sn-glycero-3-phosphocholine (DMPC)
1,2-Dipalmitoyl-sn-glycero-3-phosphocholine (DPPC)
1,2-Distearoyl-sn-glycero-3-phosphocholine (DSPC)
Phosphoethanolamines
1,2-Dilauroyl-sn-glycero-3-phosphoethanolamine (DLPE)
1,2-Dimyristoyl-sn-glycero-3-phosphoethanolamine (DMPE)
1,2-Dipalmitoyl-sn-glycero-3-phosphoethanolamine (DPPE)
1,2-Distearoyl-sn-glycero-3-phosphoethanolamine (DSPE)
Phosphoglycerols
1,2-Dilauroyl-sn-glycero-3-phosphoglycerol, sodium salt (DLPG)
1,2-Dimyristoyl-sn-glycero-3-phosphoglycerol, sodium salt (DMPG)
1,2-Dimyristoyl-sn-glycero-3-phospho-sn-1-glycerol, ammonium salt (DMP-sn-1-G,NH4)
1,2-Dipalmitoyl-sn-glycero-3-phosphoglycerol, sodium salt (DPPG,Na)
1,2-Distearoyl-sn-glycero-3-phosphoglycerol, sodium salt (DSPG,Na)
1,2-Distearoyl-sn-glycero-3-phospho-sn-1-glycerol, sodium salt (DSP-sn-1G,Na)

Phosphoserines
1,2-Dipalmitoyl-sn-glycero-3-phospho-L-serine, sodium salt (DPPS,Na)
Mixed Chain Phospholipids
1-Palmitoyl-2-oleoyl-sn-glycero-3-phosphocholine (POPC)
1-Palmitoyl-2-oleoyl-sn-glycero-3-phosphoglycerol, sodium salt (POPG,Na)
1-Palmitoyl-2-oleoyl-sn-glycero-3-phosphoglycerol, ammonium salt (POPG,NH4)
Lysophospholipids
1-Palmitoyl-2-lyso-sn-glycero-3-phosphocholine (P-lyso-PC)
1-Stearoyl-2-lyso-sn-glycero-3-phosphocholine (S-lyso-PC)
Pegylated Phospholipids
N-(Carbonyl-methoxypolyethyleneglycol 2000)—MPEG-2000-DPPE
1,2-dipalmitoyl-sn-glycero-3-phosphoethanolamine, sodium salt
N-(Carbonyl-methoxypolyethyleneglycol 5000)—MPEG-5000-DSPE
1,2-distearoyl-sn-glycero-3-phosphoethanolamine, sodium salt
N-(Carbonyl-methoxypolyethyleneglycol 5000)—MPEG-5000-DPPE
1,2-dipalmitoyl-sn-glycero-3-phosphoethanolamine, sodium salt
N-(Carbonyl-methoxypolyethyleneglycol 750)—MPEG-750-DSPE
1,2-distearoyl-sn-glycero-3-phosphoethanolamine, sodium salt
N-(Carbonyl-methoxypolyethyleneglycol 2000)—MPEG-2000-DSPE
1,2-distearoyl-sn-glycero-3-phosphoethanolamine, sodium salt The amount of phospholipids, by weight, in the emulsions of this invention may be within a range of about 0.5% to about 6%. In certain embodiments, the amount of phospholipids, by weight, may be within a range of about 1% to about 5%, or about 2% to about 4%. In certain embodiments, the amount of phospholipids is about 0.5%, 1%, 2%, 3%, 4%, 5%, or 6% by weight.

In certain embodiments, the ratio of the oil component to phospholipid in the emulsions of this invention is from about 5:1 to about 1:1 (w/w). In certain embodiments, the weight ratio is about 5:1, 4:1, 3:1, 2:1, or 1:1.

The compositions of the present invention may optionally contain additives such as acidifying, alkalizing, buffering, chelating, complexing and solubilizing agents, antioxidants and antimicrobial preservatives, suspending and/or viscosity modifying agents, tonicity modifying agents, and other biocompatible materials or therapeutic agents. Such agents generally are present in the aqueous phase of the emulsion. In certain embodiments, such additives assist in stabilizing the emulsion or the drug in the emulsion and in rendering the formulations of the present invention biocompatible.

The aqueous phase generally has an osmolality of approximately 300 mOsm and may include potassium or sodium chloride, trehalose, sucrose, sorbitol, glycerol, mannitol, polyethylene glycol, propylene glycol, albumin, amino acid and mixtures thereof. In certain embodiments, a tonicity of at least 250 mOsm is achieved with an agent that also increases viscosity, such as sorbitol or sucrose. The compounds useful for modifying osmolality of the emulsions of the present invention are referred to "tonicity modifiers" or "osmolality modifiers."

"Antioxidants" used in this invention refers primarily to metal ion chelators and/or reducing agents that are safe to use in an injectable product. A metal ion chelator functions as an antioxidant by binding to metal ions and thereby reduces the catalytic effect of metal ion on the oxidation reaction of the drug, oil or phospholipid components. Metal chelators useful in this invention include, but are not limited to, EDTA, glycine and citric acid or salts thereof.

In certain embodiments, the concentration of disodium edetate in the emulsion of this invention can be from about 0.0001% to about 1% w/v. In certain embodiments, the concentration is from about 0.001% to about 0.1% w/v, or from about 0.001% to about 0.005% w/v.

In certain embodiments, the average droplets in the emulsions of the present invention are from about 50 to about 250 nm. In certain embodiments, the average diameter of the oil droplets may be within a range of about 50 to about 200 nm, or about 75 nm to about 150 nm. In certain embodiments, the average droplet diameter is about 70, 80, 90, 100, 110, 120, 130, 140, 150, 160, 170, 180, 190 or 200 nm. In certain embodiments, the emulsions may be sterilized via 0.2 μm filters.

In certain embodiments, some or all of the components other than a taxoid drug or another water insoluble drug in the oil-in-water emulsion (e.g., an oil component, an emulsifier, a stabilizer, and a tonicity modifier) is safe, well tolerated, and acceptable by the FDA for intravenous injection.

A component of oil-in-water emulsions is regarded as "safe" if it does not cause undesired systemic or local reactions (e.g., anaphylactic shock) in patients.

A component of oil-in-water emulsions is regarded as "well tolerated" if it does not result in substantially adverse effects at the injection site, such as phlebitis, vein inflammation or vein irritation.

A component of oil-in-water emulsions is regarded as "acceptable by the FDA" if it has been used in intravenous injection products approved by the FDA as of the filing date of the present application, and is being used at a concentration comparable to those used in FDA approved products.

In certain embodiments, some or all of the components other than a taxoid drug or another water insoluble drug in the oil-in-water emulsion (e.g., an oil component, an emulsifier, a stabilizer, and a tonicity modifier) is generally regarded as safe for use in intravenous injections by a drug regulatory authority.

A component of oil-in-water emulsion is "generally regarded as safe for use in intravenous injections by a drug regulatory authority" if it has been used in intravenous injection products approved by the FDA or a drug regulatory authority in Europe as of the filing date of the present application, and is being used at a concentration comparable to those used in the products approved by the FDA in the United States or by a drug regulatory authority in Europe.

In certain embodiments, the oil-in-water emulsions of the present invention are vein non-irritable. "Vein non-irritable" refers to the property of a compound or composition, when administered intravenously, does not cause substantial irritation at the injection site, as evident by, for example, thickened skin, necrotic skin, local redness, local swelling, venous dilation with blood clog formation, or venous embolism with subcutaneous inflammation.

In certain embodiments, the present compositions are both chemically and physically stable. A composition is "chemically stable" if a taxoid drug (or another insoluble drug) in the composition is not substantially chemically degraded after storage under appropriate conditions for at least 1 month. In certain embodiments, the concentration of the intact taxoid drug (or another insoluble drug) in the composition is reduced by less than about 1%, 3%, 5%, 8%, or 10% under appropriate storage conditions (e.g., at 2-8° C. or room temperature) for at least 1, 2, 3, 4, 5, 6, 9, 12, 15, 18, or 24 months.

An emulsion composition is "physically stable" if it may be stored under appropriate conditions for at least 1 month without increase in its average droplet size by more than 100%, or evidence of phase separation, creaming, or particle aggregation. In certain embodiments, the average size of particles of a composition of the present invention does not increase by more than about 10%, 20%, 25%, 30%, 40%, 50%, 75%, or 100% under appropriate storage conditions (e.g., 2-8° C., or room temperature) for at least 1, 2, 3, 4, 5, 6, 9, 12, 15, 18, or 24 months.

In still another aspect, the present invention relates to emulsions that are ready-to-use for intravenous injection/infusion. The term "ready to use" means that the pharmaceutical compositions can be used as is or without a need for further dilution, mixing, or other alteration of its composition prior to use.

In certain embodiments, the present emulsions may be parenterally administered to a subject. "Parenteral" includes any mode of administration that does not go through the digestive tract, but excludes trans-membrane delivery such as skin patches. Parenteral administration most commonly refers to injections or infusions into blood vessels.

In certain embodiments, the mode of administration of the present emulsions is by intravenous, intra-arterial, intrathecal, intraperitoneal, intraocular, intra-articular, intramuscular or subcutaneous injection.

In certain embodiments, the oil-in-water emulsions of the present invention do not include those reconstituted from lyophilized formulations.

In certain embodiments, the emulsions of the present invention do not comprise one or more cryoprotectants or do not comprise cryoprotectant(s) in an amount sufficient for stabilizing the oil droplets of the emulsions during lyophilization (e.g., an amount sufficient for allowing the average droplet size of the rehydrated emulsion to be no more than about 200% of the average droplet size of the emulsion before the freeze-drying). In certain embodiments, the emulsions of the present invention do not comprise cryoprotectant(s) in an amount sufficient for allowing the average droplet size of the rehydrated emulsion to be no more than about 150% or about 125% of the average droplet size of the emulsion before the freeze-drying.

"Cryoprotectants" refers to those ingredients which are added to maintain the discrete and submicron droplets of the emulsion during the freeze-drying process and, upon the removal of water of the emulsion, to provide a solid matrix for the droplets to form the an oil-in-solid dispersion system. Exemplary cryoprotectants include polyols, monosaccharides, disaccharides, polysaccharides, amino acids, peptides, proteins, and hydrophilic polymers, or mixtures thereof.

Exemplary polyols include glycerin, mannitol, erythritol, maltitol, xylitol, sorbitol, polyglycitol or mixtures thereof.

Exemplary monosaccharides include glucose, mannose, fructose, lactulose, allose, altrose, gulose, idose, galactose, talose, ribose, arabinose, xylose, lyxose or mixtures thereof.

Exemplary disaccharides include sucrose, lactose, maltose, isomaltose, trehalose, cellubiose or mixtures thereof.

Exemplary polysaccharides include cellulose, amylose, inulin, chitin, chitosan, amylopectin, glycogen, pectin, hyaruronic acid or mixtures thereof.

Exemplary amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine or mixtures thereof.

Exemplary peptides include diglycine and triglycine.

Exemplary proteins include albumin, collagen, casein, and gelatin.

Exemplary hydrophilic polymers include polyethylene glycols povidones, poloxamers, polyvinyl alcohols or mixtures thereof.

In certain embodiments, the concentration of a cryoprotectant sufficient for stabilizing the oil droplets of an emulsion of the present may be in the range of about 5%, 6%, 7%, 8%, 9%, 10%, 11%, 12%, 13%, 14%, 15%, 16%, 18%, 25%, 25%, 30%, 35%, 40%, 45%, or 50% by weight.

In certain embodiments, the emulsions of the present invention do not comprise one or any of the following compounds: aliphatic or aromatic acids, amines, polyethylene glycol-linked lipids, propylene glycols, polyethylene glycols, non-ionic surfactants, polyethyleneglycol-modified phosphatidylethanolamines, tocopherols, tocotrienols, and derivatives of tocopherols and tocotrienols (see, U.S. Pat. Nos. 5,478,860; 4,816,247; 5,750,142; 5,977,172; 6,245,349; 6,348,491; and 6,458,373; published PCT Application No. WO 99/04787).

Exemplary oil-in-water emulsions may comprise: (a) a taxoid drug at a concentration of about 0.03% or higher by weight, (b) medium chain triglyceride at a concentration of about 1% to about 3% by weight, (c) soybean oil at a concentration of about 1% to about 3% by weight, (d) soy lecithin or egg lecithin at a concentration of about 1% to about 5% by weight, (e) glycine at a concentration of about 0.5 to 1% by weight, (f) glycerol at a concentration of about 1.5 to 2.5% by weight, (g) optionally EDTA at a concentration of about 0.005% by weight, and (h) water.

Other exemplary oil-in-water emulsions may comprise: (a) docetaxel at a concentration of about 0.05% by weight, (b) medium chain triglyceride at a concentration of about 1% to about 3% by weight, (c) soybean oil at a concentration of about 1% to about 3% by weight, (d) soy lecithin or egg lecithin at a concentration of about 1% to about 5% by weight, (e) glycine at a concentration of about 0.5 to 1% by weight, (f) glycerol at a concentration of about 1.5 to 2.5% by weight, (g) optionally EDTA at a concentration of about 0.005% by weight, (h) sodium chloride and/or hydrochloric acid to adjust pH to about 3.5 and 7.0, and (i) water.

Other exemplary oil-in-water emulsions may comprise: (a) paclitaxel at a concentration of about 0.05% by weight, (b) medium chain triglyceride at a concentration of about 1% to about 3% by weight, (c) soybean oil at a concentration of about 1% to about 3% by weight, (d) soy lecithin or egg lecithin at a concentration of about 1% to about 5% by weight, (e) glycine at a concentration of about 0.5 to 1% by weight, (e glycerol at a concentration of about 1.5 to 2.5% by weight, (g) optionally EDTA at a concentration of about 0.005% by weight, (h) sodium chloride and/or hydrochloric acid to adjust pH to about 6 and 7, and (i) water.

Other exemplary oil-in-water emulsions may comprise: (a) docetaxel at a concentration of about 0.05% by weight, (b) soybean oil at a concentration of about 1% to about 6% by weight, (c) soy lecithin or egg lecithin at a concentration of about 1% to about 5% by weight, (d) glycine at a concentration of about 0.5 to 1% by weight, (e) glycerol at a concentration of about 1.5 to 2.5% by weight, (f) optionally EDTA at a concentration of about 0.005% by weight, (g) sodium chloride and/or hydrochloric acid to adjust pH to about 3.5 and 7.0, and (h) water.

Other exemplary oil-in-water emulsions may comprise: (a) paclitaxel at a concentration of about 0.05% by weight, (b) soybean oil at a concentration of about 1% to about 6% by weight, (c) soy lecithin or egg lecithin at a concentration of about 1% to about 5% by weight, (d) glycine at a concentration of about 0.5 to 1% by weight, (e) glycerol at a concentration of about 1.5 to 2.5% by weight, (f) optionally EDTA at a concentration of about 0.005% by weight, (g) sodium chloride and/or hydrochloric acid to adjust pH to about 6 and 7, and (h) water.

The present invention also provides methods for preparing oil-in-water emulsions for delivering taxoid drugs and other water insoluble drugs as described herein. Such emulsion may be prepared by (a) forming a mixture that comprises appropriate amounts of (i) a taxoid drug (or another water insoluble drug), (ii) an oil component (e.g., a vegetable oil, or a combination of a vegetable oil and a medium chain triglyceride), and (iii) a phospholipid, and (b) forming an oil-in-water emulsion with the mixture of step (a) and an aqueous solution. The methods may further comprise one or more of the following steps: (A) adjusting the pH of the emulsion to a desirable range, (B) homogenizing with high shear the emulsion to provide an emulsion with an average droplet diameter less than about 200 nm, and (C) sterilizing the emulsion by filtration using a 0.2 μm filter.

An exemplary method for preparing the emulsions of the present invention may comprise one or more of the following steps:

(1) Dissolve the drug, oil, and emulsifier in a sufficient amount of a volatile solvent, such as ethanol, methylene chloride, chloroform, isopropanol, methanol, tert-butylalcohol, etc., to form a clear solution, (2) Remove the solvent to a toxicologically acceptable residual level by vacuum or by blowing solution with a nitrogen or air stream to obtain an oil phase, (3) Dissolve the tonicity modifier, preservatives cryoprotectant(s), and/or other inactive ingredients in water to form an aqueous phase, (4) Optionally filter, separately, the oil and/or aqueous phase to remove particles, (5) Add the aqueous phase to the oil phase, and mix well to form a crude oil-in-water emulsion, (6) Adjust pH of the crude emulsion to the desired pH range, (7) Pass the crude emulsion through a high pressure homogenizer, such as a Microfluidizer (e.g. Model 110F by Microfluidics Corp, MA) equipped with an emulsion interaction chamber operating at approximately 18,000-23,000 psi pressure for 2 to 10 passages until the emulsion droplets reach the desired average size range and the emulsion is free of droplets of greater than 5 microns in diameter, (8) Aseptically pass the emulsion through a sterile 0.2 micron-rated membrane filter to sterilize the emulsion, (9) Aseptically fill the filtered emulsion into appropriate sterile containers and seal the containers with appropriate sterile stoppers, and

(10) Perform necessary tests on the final emulsion.

The present invention also provides methods for using the compositions described herein. For instance, the present invention provides methods for treating cancer that comprise administering to a patient in need thereof compositions that comprise insoluble anti-neoplastic drugs (e.g., paclitaxel or docetaxel).

The following examples are intended to illustrate the invention without limiting the practice thereof.

EXAMPLES

Example 1

A paclitaxel low oil emulsion (3.1% oil content, Table 1.1) was prepared as described below.

TABLE 1.1

| Component | % (w/w) |
|---|---|
| Paclitaxel | 0.050 |
| Soybean oil (Super refined ™ by Croda) | 1.550 |
| Medium chain triglyceride (Miglyol ™ 812 by Sasol) | 1.550 |
| Egg lecithin (LIPOID ™ E80 by Lipoid) | 3.10 |
| Glycerin | 2.25 |
| Glycine | 0.5 |
| Sodium hydroxide or hydrochloric acid to adjust pH to | 6-7 |
| Water for Injection | Add to 100 |

The 3.1% oil emulsion was prepared by combining and mixing paclitaxel, soybean oil, medium chain triglyceride, egg lecithin and sufficient amount of ethanol to form a clear yellow solution. The solution was dried under vacuum using a rotary evaporator until the residual ethanol content is less than 2% of the combined weight of the other components to obtain a thick yellow liquid (i.e., the oil phase). Glycerin and glycine were weighed out and dissolved in appropriate amount of water to form an aqueous phase. The aqueous phase was added to the oil phase, and the mixture was agitated using a high shear mixer (e.g. Ultra Turrax by Tekmar Company) to obtain a crude emulsion. The pH of the crude emulsion was adjusted to 6.5±0.2 using 1N NaOH or 1N HCl solution. The pH adjusted crude emulsion was passed 5 times through a microfluidzer (Model 110F by microfluidics) equipped with an emulsion interaction chamber at an operation pressure of 18,000-23,000 psi. The resulting emulsion was filtered through a sterile 0.2 micron filter, and the filtered emulsion was then filled into glass vials, which was then sealed with rubber closures. The final low oil emulsion was a translucent light yellow liquid.

A study was conducted to evaluate the stability of paclitaxel (chemical stability) in this 3.1% oil emulsion and the stability of the emulsion itself (physical stability). The chemical stability was determined based on concentration of paclitaxel in the emulsion over time. The paclitaxel concentrations in the emulsion were determined by a reversed phase high-pressure liquid chromatography (Hewlett Parkard Model 1050 HPLC). The physical stability was evaluated based on the average oily droplet diameter and the number of large droplets (which are more than 5 microns). The average oil droplet diameter was measured using a laser light scattering spectrometer (Model 370 Submicron Particle Sizer by Particle Sizing System, Santa Barbara, Calif.); the large droplets were counted under an optical microscope with a hemacytometer (Bright-Line by Hausser Scientific, PA).

The physical stability data of this emulsion are shown in Table 1.2.

TABLE 1.2

| Storage | Duration | Average droplet diameter (nm) | Counts of large droplets (>5 micron) |
|---|---|---|---|
| | Initial | 100 | None |
| −20° C. | 3 weeks | — | — |
| | 10 weeks | >300 | Many |
| 5° C. | 3 weeks | 110 | None |
| | 10 weeks | 110 | None |
| 25° C. | 3 weeks | 101 | None |
| | 10 weeks | 115 | None |
| 40° C. | 3 weeks | 123 | None |
| | 10 weeks | 210 | None |

The chemical stability data are shown in Table 1.3.

TABLE 1.3

| Storage | Duration | Paclitaxel Concentration (mg/mL) (% recovery of the initial value) |
|---|---|---|
| | Initial | 0.465 (100) |
| −20° C. | 3 weeks | — |
| | 10 weeks | 0.469 (101) |
| 5° C. | 3 weeks | — |
| | 10 weeks | 0.465 (100) |
| 25° C. | 3 weeks | — |
| | 10 weeks | 0.470 (101) |
| 40° C. | 3 weeks | 0.450 (97) |
| | 10 weeks | 0.448 (96) |

The data in Tables 1.2 and 1.3 indicate that the fresh 3.1% oil emulsion has a very small average droplet size (100 nm)

and was free of large droplets (larger than 5 microns). Under the normal storage condition (5° C. and 25° C.), the emulsion maintained such small droplet size for an extensive period of time (10 weeks) without any formation of the large droplet (larger than 5 micron). Paclitaxel is also stable in the emulsion; no detectable loss of the drug was observed after 10 weeks at 5° C. or 25° C. Overall, this low-oil emulsion has shown excellent stability with a very small droplet size.

Example 2

Three other low oil emulsions were prepared using similar method of preparation and were evaluated for long-term stability using the same testing methods as described in Example 1.

TABLE 2.1

| 1.85% oil emulsion | |
|---|---|
| Component | % w/w |
| Paclitaxel | 0.03 |
| Miglyol 812 | 1.85 |
| Soy lecithin (Phospholipon ™ 90G by Phospholipid) | 1.85 |
| Ethanol | 0.80 |
| Glycerol | 2.63 |
| Propylene glycol | 0.38 |
| Sodium hydroxide or hydrochloric acid to adjust pH to | 6-7 |
| Water for Injection | Add to 100 |

TABLE 2.2

| 2.47% oil emulsion | |
|---|---|
| Component | % w/w |
| Paclitaxel | 0.04 |
| Miglyol 812 | 2.47 |
| Soy lecithin (Phospholipon ™ 90G by Phospholipid) | 2.47 |
| Ethanol | 1.06 |
| Glycerol | 3.50 |
| Propylene glycol | 0.50 |
| Sodium hydroxide or hydrochloric acid to adjust pH to | 6-7 |
| Water for Injection | Add to 100 |

TABLE 2.3

| 3.09% oil emulsion | |
|---|---|
| Component | % w/w |
| Paclitaxel | 0.05 |
| Miglyol 812 | 3.09 |
| Soy lecithin (Phospholipon ™ 90G by Phospholipid) | 3.09 |
| Ethanol | 1.33 |
| Glycerol | 4.39 |
| Propylene glycol | 0.63 |
| Sodium hydroxide or hydrochloric acid to adjust pH to | 6-7 |
| Water for Injection | Add to 100 |

The physical stability data from the emulsion droplet size measurement are listed in Table 2.4 and chemical stability data in Table 2.5.

TABLE 2.4

| | | Average droplet diameter (nm) Counts of the large droplets (>5 micron) | | |
|---|---|---|---|---|
| Storage | Duration | 1.85% oil emulsion | 2.47% oil emulsion | 3.09% oil emulsion |
| | 0 | 149.5 (None) | 163.7 (None) | 166.8 (None) |
| 25° C. | 6 days | 150.0 (None) | 159.1 (None) | 167.2 (None) |
| | 14 days | 154.1 (None) | 163.0 (None) | 175.4 (None) |
| | 21 days | 174.3 (None) | 168.3 (None) | 188.1 (None) |
| | 28 days | 161.1 (None) | 182.2 (None) | 196.2 (None) |
| 5° C. | 9 months | 145.4 (None) | 160.6 (None) | 168.1 (None) |

TABLE 2.5

| | | Paclitaxel concentration (mg/mL) | | | pH | | |
|---|---|---|---|---|---|---|---|
| Storage | Duration | 1.85% oil emulsion | 2.47% oil emulsion | 3.09% oil emulsion | 1.85% oil emulsion | 2.47% oil emulsion | 3.09% oil emulsion |
| | Initial | 0.331 | 0.434 | 0.504 | — | — | — |
| 5° C. | 2 weeks | 0.324 | 0.475 | 0.493 | — | — | — |
| | 4 weeks | 0.360 | 0.450 | 0.510 | 6.92 | 7.08 | 7.19 |
| | 10 weeks | 0.339 | 0.467 | 0.524 | 6.99 | 6.28 | 7.00 |
| | 16 weeks | 0.360 | 0.448 | 0.506 | — | — | — |
| | 9 months | 0.337 | 0.420 | 0.473 | — | — | — |
| 25° C. | 2 weeks | 0.331 | 0.459 | 0.508 | — | — | — |
| | 4 weeks | 0.345 | 0.473 | 0.520 | 6.96 | 7.17 | 6.66 |
| | 10 weeks | 0.362 | 0.472 | 0.516 | 6.32 | 6.48 | 6.56 |
| | 16 weeks | 0.359 | 0.431 | 0.414 | — | — | — |
| 40° C. | 2 weeks | 0.357 | 0.477 | 0.501 | — | — | — |
| | 4 weeks | 0.323 | 0.491 | 0.485 | 5.83 | 6.35 | 6.33 |
| | 10 weeks | 0.244 | 0.436 | 0.351 | 3.75 | 3.84 | 3.49 |
| | 16 weeks | 0.040 | 0.098 | 0.058 | — | — | — |

In conclusion, the three low oil emulsions (1.85%, 2.47% and 3.09% total oil content) disclosed in this example exhibited excellent stability.

Example 3

To demonstrate the superior stability of low oil emulsions compared to high oil emulsions (i.e., emulsions with total oil content higher than 10%), the oil phase of Example 1 was mixed with an aqueous phase at different ratios to obtain the final emulsions containing 31%, 15.5% and 10.3% oil as shown in Table 3.1. The method of preparations was the same as described in Example 1.

TABLE 3.1

| | High oil emulsions | | |
|---|---|---|---|
| Component | 31% oil emulsion %(w/w) | 15.5% oil emulsion %(w/w) | 10.3% oil emulsion %(w/w) |
| Paclitaxel | 0.50 | 0.25 | 0.17 |
| Soybean oil (Super refined ™ by Croda) | 15.5 | 7.75 | 5.16 |
| Medium chain triglyceride (Miglyol ™ 812 by Sasol) | 15.5 | 7.75 | 5.16 |
| Egg lecithin (LIPOID ™ E80 by Lipoid) | 31.0 | 15.5 | 10.3 |
| Glycerin | 2.5 | 2.5 | 2.5 |
| Glycine | 0.5 | 0.5 | 0.5 |
| Sodium hydroxide or hydrochloric acid to adjust pH to | 6-7 | 6-7 | 6-7 |
| Water for Injection | Add to 100 | Add to 100 | Add to 100 |

The final emulsions prepared according to Table 3.1 were very thick, creamy and contained many large droplets/particles. These creamy emulsions could not be filtered through 0.2-micron filters and are not injectable. This example indicates that a low oil concentration was essential for having an emulsion of small droplet size and good stability. By proportionally increasing the oil content to 10% or above, the emulsion formed are no longer acceptable as a safe parenteral drug delivery vehicle.

Example 4

A low-oil (3.1%) emulsion of docetaxel was prepared according to Table 4.1 using the same method as described in Example 1. Docetaxel is more stable at an acidic pH, therefore the pH of the emulsion was adjusted to pH 4-7.0. The droplet size and docetaxel stability data are similar to what was reported in Example 1.

TABLE 4.1

| 3.1% oil emulsion of docetaxel | |
|---|---|
| Component | %(w/w) |
| Docetaxel | 0.050 |
| Soybean oil (Super refined ™ by Croda) | 1.550 |
| Medium chain triglyceride (Miglyol ™ 812 by Sasol) | 1.550 |
| Egg lecithin (LIPOID ™ E80 by Lipoid) | 3.10 |
| Glycerin | 1.75 |
| Glycine | 0.5 |
| Sodium hydroxide or hydrochloric acid to adjust pH to | 4-4.5 |
| Water for Injection | Add to 100 |

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A sterile injectable oil-in-water emulsion comprising:
   (a) paclitaxel at a concentration selected from the group consisting of 0.03%, 0.04%, and 0.05% by weight,
   (b) an oil component at a concentration from 1% to 4% by weight, wherein the oil component comprises a vegetable oil or a medium chain triglyceride, or a mixture thereof,
   (c) a phospholipid component at a concentration from 1% to 4% by weight, wherein the weight ratio of the oil component to the phospholipid component is about 1:1,
   (d) sodium hydroxide and/or hydrochloric acid to adjust the pH to between about 6 and 7, and
   (e) water, wherein said injectable oil-in-water emulsion has an average oil droplet diameter in a range of 75 nm to 150 nm, is sterilized by filtration using a 0.2 μm filter, does not include a cryoprotectant or protein, and is stable for at least 18 months.

2. The injectable emulsion of claim 1 wherein paclitaxel is at a concentration of about 0.05% by weight.

3. The injectable emulsion of claim 1 wherein the vegetable oil is soybean oil.

4. The injectable emulsion of claim 1 wherein the phospholipid component comprises soy lecithin or egg lecithin.

5. The injectable emulsion of claim 1 further comprising a stabilizer.

6. The injectable emulsion of claim 5 wherein the stabilizer is ethylene diamine-tetraacetic acid (EDTA).

7. The injectable emulsion of claim 6 wherein the concentration of EDTA is from about 0.001% to about 0.01% by weight.

8. The injectable emulsion of claim 1 further comprising a tonicity modifier.

9. The injectable emulsion of claim 1 wherein the average size of the oil droplets in the emulsion does not increase more than 25% after storage at about 2-8° C. for 6 months.

10. The injectable emulsion of claim 1 wherein the concentration of paclitaxel in the emulsion does not decrease by more than 10% after storage at about 2-8° C. for 6 months.

11. A sterile injectable oil-in-water emulsion comprising:
   (a) docetaxel at a concentration selected from the group consisting of 0.03%, 0.04% and 0.05% by weight,
   (b) an oil component at a concentration from 1% to 4% by weight, wherein the oil component comprises a vegetable oil or a medium chain triglyceride, or a mixture thereof,
   (c) a phospholipid component at a concentration from 1% to 4% by weight, wherein the ratio of the oil component to the phospholipid component is about 1:1, and
   (d) water, wherein said injectable oil-in-water emulsion has an average oil droplet diameter in a range of 75 nm to 150 nm, is sterilized by filtration using a 0.2 μm filter, does not include a cryoprotectant or protein, and is stable for at least 18 months.

12. The injectable emulsion of claim 11 further comprising:
   (a) docetaxel at a concentration of 0.05% by weight,
   (b) the medium chain triglyceride at a concentration from 1% to 3% by weight,
   (c) the vegetable oil is soybean oil at a concentration from 1% to 3% by weight, (d) the phospholipid component is soy lecithin or egg lecithin at a concentration from 1% to 5% by weight, and
(e) optionally EDTA at a concentration of 0.005% by weight.

13. A sterile injectable oil-in-water emulsion consisting essentially of:
(a) paclitaxel at a concentration selected from the group consisting of 0.03%, 0.04% and 0.05% by weight;
(b) an oil component at a concentration from 1% to 4% by weight, wherein the oil component comprises a vegetable oil or a medium chain triglyceride, or a mixture thereof;
(c) a phospholipid component at a concentration from 1% to 4% by weight, wherein the weight ratio of the oil component to the phospholipid component is about 1:1;
(d) sodium hydroxide and/or hydrochloric acid to adjust the pH to between about 6 and 7, and
(e) water, wherein said injectable oil-in-water emulsion has an average oil droplet diameter in a range of 75 nm to 150 nm, is sterilized by filtration using a 0.2 µm filter, does not include a cryoprotectant or protein, and is stable for at least 18 months.

14. The injectable emulsion of claim 13, wherein paclitaxel is at a concentration of about 0.05% by weight.

15. The injectable emulsion of claim 13, wherein the vegetable oil is soybean oil.

16. The injectable emulsion of claim 13, wherein the phospholipid component comprises soy lecithin or egg lecithin.

17. A sterile injectable oil-in-water emulsion consisting essentially of:
(a) paclitaxel at a concentration selected from the group consisting of 0.03%, 0.04% and 0.05% by weight;
(b) an oil component at a concentration from 1% to 4% by weight, wherein the oil component comprises a vegetable oil or a medium chain triglyceride, or a mixture thereof;
(c) a phospholipid component at a concentration from 1% 4% by weight, wherein the weight ratio of the oil component to the phospholipid component is about 1:1;
(d) sodium hydroxide and/or hydrochloric acid to adjust the pH to between about 6 and 7;
(e) a stabilizer; and
(f) water, wherein said injectable oil-in-water emulsion has an average oil droplet diameter in a range of 75 nm to 150 nm, is sterilized by filtration using a 0.2 µm filter, does not include a cryoprotectant or protein, and is stable for at least 18 months.

18. The injectable emulsion of claim 17, wherein the stabilizer is ethylene diamine-tetraacetic acid (EDTA).

19. The injectable emulsion of claim 18, wherein the concentration of EDTA is from about 0.001% to about 0.01% by weight.

20. A sterile injectable oil-in-water emulsion consisting essentially of:
(a) paclitaxel at a concentration selected from the group consisting of 0.03%, 0.04% and 0.05% by weight;
(b) an oil component at a concentration from 1% to 4% by weight, wherein the oil component comprises a vegetable oil or a medium chain triglyceride, or a mixture thereof;
(c) a phospholipid component at a concentration from 1% to 4% by weight, wherein the weight ratio of the oil component to the phospholipid component is about 1:1;
(d) sodium hydroxide and/or hydrochloric acid to adjust the pH to between about 6 and 7;
(e) a tonicity modifier; and
(f) water, wherein said injectable oil-in-water emulsion has an average oil droplet diameter in a range of 75 nm to 150 nm, is sterilized by filtration using a 0.2 µm filter, does not include a cryoprotectant or protein, and is stable for at least 18 months.

21. The injectable emulsion of claim 13, wherein the average size of the oil droplets in the emulsion does not increase more than 25% after storage at about 2-8° C. for 6 months.

22. The injectable emulsion of claim 13, wherein the concentration of paclitaxel in the emulsion does not decrease by more than 10% after storage at about 2-8° C. for 6 months.

23. A sterile injectable oil-in-water emulsion consisting essentially of:
(a) docetaxel at a concentration selected from the group consisting of 0.03%, 0.04% and 0.05% by weight,
(b) an oil component at a concentration from 1% to 4% by weight, wherein the oil component comprises a vegetable oil or a medium chain triglyceride, or a mixture thereof,
(c) a phospholipid component at a concentration from 1% to 4% by weight, wherein the ratio of the oil component to the phospholipid component is about 1:1, and
(d) water, wherein said injectable oil-in-water emulsion has an average oil droplet diameter in a range of 75 nm to 150 nm, is sterilized by filtration using a 0.2 µm filter, does not include a cryoprotectant or protein, and is stable for at least 18 months.

24. A sterile injectable oil-in-water emulsion consisting essentially of:
(a) docetaxel at a concentration of 0.05% by weight,
(b) an oil component at a concentration from 1% to 3% by weight, wherein the oil component is a medium chain triglyceride;
(c) a phospholipid component at a concentration from 1% to 4% weight, wherein the ratio of the oil component to the phospholipid component is about 1:1, wherein the phospholipid component is soy lecithin or egg lecithin;
(d) water; and
(e) optionally EDTA at a concentration of about 0.005% by weight, wherein said injectable oil-in-water emulsion has an average oil droplet diameter in a range of 75 nm to 150 nm, is sterilized by filtration using a 0.2 µm filter, does not include a cryoprotectant or protein, and is stable for at least 18 months.

* * * * *